(12) United States Patent
Thalhammer et al.

(10) Patent No.: US 8,227,638 B2
(45) Date of Patent: Jul. 24, 2012

(54) PROCESS FOR PREPARING CREATINE, CREATINE MONOHYDRATE OR GUANIDINOACETIC ACID

(75) Inventors: Franz Thalhammer, Trostberg (DE); Thomas Gastner, Engelsberg (DE)

(73) Assignee: AlzChem Trostberg GmbH, Trostberg (DE)

( * ) Notice: Subject to any disclaimer, the term of this patent is extended or adjusted under 35 U.S.C. 154(b) by 586 days.

(21) Appl. No.: 12/226,040

(22) PCT Filed: Apr. 5, 2007

(86) PCT No.: PCT/EP2007/003121
§ 371 (c)(1),
(2), (4) Date: Oct. 6, 2008

(87) PCT Pub. No.: WO2007/115799
PCT Pub. Date: Oct. 18, 2007

(65) Prior Publication Data
US 2009/0163739 A1 Jun. 25, 2009

(30) Foreign Application Priority Data
Apr. 6, 2006 (DE) .......... 10 2006 016 227

(51) Int. Cl.
*C07C 51/295* (2006.01)
*C07C 279/10* (2006.01)
(52) U.S. Cl. ........... 562/539; 562/560
(58) Field of Classification Search .......... None
See application file for complete search history.

(56) References Cited

U.S. PATENT DOCUMENTS

| | | | |
|---|---|---|---|
| 2,761,807 A * | 9/1956 | Borsook et al. | 514/430 |
| 5,220,054 A | 6/1993 | Urano et al. | |
| 5,719,319 A * | 2/1998 | Weiss et al. | 562/560 |
| 5,739,390 A | 4/1998 | Franczyk et al. | |
| 6,326,513 B1 * | 12/2001 | An et al. | 562/560 |
| 6,706,662 B2 * | 3/2004 | Morgenstern et al. | 502/345 |

FOREIGN PATENT DOCUMENTS

| | | |
|---|---|---|
| DE | 199 20 962 A1 | 11/2000 |
| EP | 0 513 396 A1 | 11/1992 |
| EP | 1 382 390 A1 | 1/2004 |

OTHER PUBLICATIONS

Benzi et al, Journal of Sports Medicine and Physical Fitness, Creatine as Nutritional Supplementation and Medicinal Product, 2001, 41(1), pp. 1-10.*

* cited by examiner

*Primary Examiner* — Paul A Zucker
(74) *Attorney, Agent, or Firm* — Fulbright & Jaworski L.L.P.

(57) ABSTRACT

A process for producing creatine, creatine monohydrate or guanidinoacetic acid is proposed, wherein firstly N-methylethanolamine or ethanolamine is catalytically dehydrogenated in each case in alkaline solution and the sarcosinate or glycinate solutions that are obtained in this manner are finally reacted under acidic conditions with a guanylating agent such as for example O-alkylisourea or cyanamide. In this manner products are obtained in high yields and very good purity where in contrast to the prior art no traces whatsoever of hydrocyanic acid, formaldehyde, chloroacetic acid or ammonia are present. The formation of the toxicologically critical dihydrotriazine is also avoided.

24 Claims, No Drawings

PROCESS FOR PREPARING CREATINE, CREATINE MONOHYDRATE OR GUANIDINOACETIC ACID

This application is a §371 of PCT/EP2007/003121 filed Apr. 5, 2007, which claims priority from German Patent Application No. 10 2006 016 227.7 filed Apr. 6, 2006.

The present invention concerns a process for producing creatine, creatine monohydrate or guanidinoacetic acid.

Guanidinoacetic acid and creatine are endogenous substances which occur in animals and also in humans where guanidinoacetic acid is the direct metabolic precursor of creatine. Creatine plays an important role in the energy metabolism of the cell. In the body phosphorylation of creatine results in the formation of phosphocreatine which, in addition to adenosine triphosphate (ATP), is an important energy reserve of muscle. Creatine and guanidinoacetic acid can be formed endogenously and can also be taken up from food which is why creatine has been known for a long time as a suitable food supplement and animal feed. Guanidinoacetic acid has also already been used advantageously as an animal feed for breeding animals and fattening animals to increase the fattening performance and improve the feed utilization (WO 2005/120246 A1). Intense and prolonged muscular work rapidly exhausts the creatine stores that are naturally present in the body. For this reason targeted creatine doses have a positive effect on endurance and performance especially in competitive athletes.

Syntheses for producing creatine and guanidinoacetic acid were already developed in the $19^{th}$ century. Strecker was the first to describe the synthesis of guanidinoacetic acid from glycine and cyanamide (Strecker, M. "Jahresbericht Fortschr. Chem. Verw"., (1861), 530). In an analogous manner he subsequently also obtained creatine by reacting sarcosine with cyanamide in aqueous solution (Strecker, "Jahresber. über die Fortschritte der Chemie, (1868), 686).

A process for producing creatine by reacting cyanamide with sodium or potassium sarcosinate is described in EP 0 754 679 B1. In this case the reaction is carried out in water or in a mixture of water and an organic solvent at a temperature of 20 to 150° C. and a pH of 7.0 to 14.0. An organic or inorganic acid, preferably hydrochloric acid, acetic acid or formic acid is used to adjust the pH.

U.S. Pat. No. 6,326,513 describes the reaction of sarcosine or sodium sarcosinate with S-methylthiourea or with S-methylthiourea sulfate in water or a mixture of water and an alcohol. A reaction temperature of 15 to 140° C. is envisaged; the pH is 7.0 to 13.0.

DE 199 20 962 A1 concerns the adjustment of the pH of a sarcosine-containing solution by bipolar electrodialysis. In this process the solution that is prepared is preferably adjusted to a pH of 9 to 10 and can subsequently be reacted with cyanamide to form creatine or creatine monohydrate.

Furthermore, the patent CN 1240207 describes the production of a sarcosinate solution from chloroacetic acid and methylamine. In order to produce creatine the sarcosine hydrochloride that is obtained is adjusted to a pH of 9-12 with sodium hydroxide solution and ammonia and reacted with cyanamide.

The production of sodium sarcosinate by a Strecker synthesis has been known for a long time. Thus, DE 25 03 582 A1 describes the reaction of methylamine, formaldehyde and hydrocyanic acid at 18° C. and the subsequent saponification of the resulting sarcosine nitrile with sodium hydroxide solution or potassium hydroxide solution at 50-55° C.

The preparation of aqueous solutions of sodium salts of the amino acids glycine and sarcosine by a catalytic dehydrogenation reaction of the corresponding amino-alcohols ethanolamine or N-methylethanolamine is known. According to the state of the art the dehydrogenation of aminoalcohols is carried out in an aqueous, alkaline solution on a copper-containing catalyst at elevated temperature and under pressure. The hydrogen that is formed during the reaction is discharged from the reactor during this process in order to keep the pressure constant. Different types of catalysts are used for the reaction where a common feature of all them is that they contain copper as the active element. Thus, the US Application US 2002-038,051 describes the use of Raney copper which is preferably doped with other metals and in particular noble metals. Sodium glycinate is obtained in this process with a yield of >98%. The production of sodium sarcosinate is also reported.

The U.S. Pat. No. 6,159,894 claims the use of a catalyst based on copper and zirconium which is optionally doped with other metals in order to produce aminocarboxylic acids from aminoalcohols.

The Application WO 98/50150 A1 concerns the dehydrogenation of inter alia ethanolamines on a copper-based catalyst on an inert support such as active carbon.

The use of a reaction solution of Na sarcosinate or Na glycinate obtained according to the prior art from a dehydrogenation process to produce creatine or guanidinoacetic acid is hitherto unknown.

The sodium sarcosinate or sarcosine solutions or sodium glycinate and glycine solutions used according to the prior art to produce creatine, creatine monohydrate and guanidinoacetic acid are produced by the Strecker process or they are produced from chloroacetic acid and methylamine or ammonia and usually contain characteristic impurities such as hydrocyanic acid, formaldehyde, chloroacetic acid, iminodiacetic acid, methyliminodiacetic acid, ammonia and methylamine. However, this spectrum of impurities results in problems in the production process of creatine, creatine monohydrate and guanidinoacetic acid because these compounds or secondary products thereof such as dihydrotriazine can remain in the final product as impurities and are toxicologically critical.

Hence, the object of the present invention was to develop a new process which does not have the said disadvantages of the prior art but rather enables the production of creatine, creatine monohydrate and guanidinoacetic acid in the highest yields and purities.

The object is achieved according to the invention by $a_1$) dehydrogenating N-methyl-ethanolamine in alkaline solution on a catalyst to form sodium sarcosinate or $a_2$) dehydrogenating ethanolamine in alkaline solution on a catalyst to form sodium glycinate, subsequently b) adjusting the sodium sarcosinate solution obtained in this manner from $a_1$) or the sodium glycinate solution obtained from $a_2$) to a pH of 7.0 to 13.0 by an acid or by bipolar electrodialysis and reacting the sarcosine or glycine obtained in this manner with a guanylating agent.

It has surprisingly turned out that the described problems in the prior art can be circumvented with sodium sarcosinate or sodium glycinate which have been produced by catalytic dehydrogenation of methylethanolamine or ethanolamine. The formation of hydrocyanic acid, formaldehyde, chloroacetic acid and ammonia or methylamine is completely avoided. It has surprisingly also turned out that the formation of dihydrotriazine is no longer observed in the creatine production when catalytically-produced sodium sarcosinate is used. Furthermore, the contamination of the final products with iminodiacetic acid or methyliminodiacetic acid is considerably reduced. These advantages were unexpected in their entirety.

The invention concerns in particular a process for producing creatine, creatine monohydrate or guanidinoacetic acid wherein firstly N-methylethanolamine or ethanolamine is catalytically dehydrogenated in each case in alkaline solution and the sarcosinate or glycinate solutions that are obtained in this manner are finally reacted under acidic conditions with a guanylating agent such as for example O-alkylisourea or cyanamide. In this manner products are obtained in high yields and very good purity where in contrast to the prior art no traces whatsoever of hydrocyanic acid, formaldehyde, chloroacetic acid or ammonia are present. The formation of the toxicologically critical dihydrotriazine is also avoided.

The copper-containing catalysts known from the prior art are suitable for the catalytic dehydrogenation of ethanolamine and methylethanolamine according to process step a). They can also be doped with other metals such as nickel, palladium or platinum. However, pure nickel, palladium or platinum catalysts are also very suitable and the catalysts can also each be used in a supported form. The reaction is carried out at temperatures between 120 and 220° C., where pressures between 0.01 and 30 bar, preferably between 0.1 and 20 bar and particularly preferably between 1.0 and 10 bar are advisable. It is advantageous to work in aqueous solutions in which case the concentrations of methylethanolamine or ethanolamine are usually selected for economic reasons such that a 20 to 60% solution of the product is present after the reaction according to steps $a_1$) or $a_2$). Solutions having a concentration between 30 and 45% are regarded as particularly preferred. All percentages as used herein refer to the weight if not stated otherwise.

It is advantageous to separate the catalyst before the subsequent reaction step b) because the final reaction with a guanylating agent in the described concentration range results in a precipitation of the product that is formed.

Nitric acid, phosphoric acid, acetic acid, hydrochloric acid, sulphuric acid and/or carbon dioxide are suitable for subsequently adjusting the pH of the sodium sarcosinate or sodium glycinate solutions that are obtained to values between 7 and 13. Alternatively the pH can also be adjusted with the aid of a bipolar electrodialysis. The base that is formed in this process can be fed back into the first process step which is also taken into consideration by the present invention.

O-Alkylisourea and S-alkylthiourea or salts thereof are advantageously used to guanylate the sarcosine solution obtained from step $a_1$) or the glycine solution obtained from the step $a_2$). Furthermore, cyanamide can also be used as a guanylating agent. According to the present invention the guanylation can be carried out in a temperature range of 10° C. to 120° C., preferably between 20 and 80° C. and at pressures of 0.1 to 10 bar, preferably of 1.0 to 5.0 bar. It is regarded as preferable within the scope of the invention to select a ratio of sodium sarcosinate or sarcosine or sodium glycinate or glycine to guanylating agent between 1:0.1 to 2.0. The ratio is preferably 1:1 to 1.1.

The described process can also be carried out without isolating the intermediate products that are formed; it is also suitable for being conducted as a continuous process.

The resulting product in the form of creatine or guanidinoacetic acid is obtained as a suspension and can be separated from the liquid phase by any commonly used method. The crystals that are obtained are subsequently preferably washed with an aqueous medium and dried. Depending on the drying procedure, creatine or creatine monohydrate is obtained. In contrast guanidinoacetic acid does not form a stable monohydrate.

Overall it has been shown that the desired reaction product is not only obtained in high yields and very good purity using the process according to the invention according to the problem to be solved, but also that in particular the space/time yields are extremely good which makes the process very economic combined with a simplified process procedure.

The following examples illustrate the breadth of the present invention.

EXAMPLES

Example 1

Preparation of an Na Sarcosinate Solution 10 g (calculated on the basis of the dry substance) of a Cu/Ni-based Raney catalyst (Degussa AG, BOO 111) was placed first as a suspension in water in a 600 ml autoclave with stirrer, pressure control valve and jacket heating and 75 g N-methyl-ethanolamine as well as 204 g of a 20% by weight sodium hydroxide solution were added. The autoclave was closed and the contents were heated to a temperature of 160° C. with the aid of the jacket heating. An increasing pressure of hydrogen was generated in this process which was kept at 10 bar (absolute) by the controlled opening of the pressure control valve. The release of gas was completely finished after 4 hours and the reactor was cooled to 90° C. After the stirrer was switched off, the catalyst sedimented within one hour and a portion of the supernatant clear solution of Na sarcosinate was moved from the autoclave through a plunge pipe. The catalyst remained in the reactor and could be used again in further batches.

For each further cycle the suspension of catalyst remaining in the reactor was admixed with the said amounts of N-methylethanolamine and sodium hydroxide solution and the reaction was started by heating.

With the exception of the initial batch, 270 g of a colourless solution of Na sarcosinate containing 40.0% by weight (corresponds to a yield of 97.2% of theory) was obtained per cycle.

Example

Preparation of a Solution of Na Glycinate 10 g (calculated on the basis of the dry substance) of a Pd-doped copper catalyst on active carbon (Degussa AG, CE 1015 OY/W) suspended in water was placed first analogously to example 1 in an autoclave and 61 g ethanolamine and 272 g sodium hydroxide solution (15% by weight) were added. The autoclave was closed and the contents were heated to 160° C. The pressure was kept at 12 bar (absolute) and the hydrogen that formed was continuously discharged by a pressure control valve. After the end of the reaction (which is evident from the decrease in gas release) it was cooled to 90° C. and the catalyst was removed from the product solution by filtration. 315 g filtrate which contained 29.8 g % by weight Na glycinate was obtained (corresponds to a yield of 96.7% of theory).

The filtered catalyst was suspended in 10 g water and fed back into subsequent batches.

Example 3

Preparation of Creatine Monohydrate 4625 g (16.7 mol) of a 40% by weight sodium sarcosinate solution prepared according to example 1 was added first. A pH of 9.6 (at 20° C.) was adjusted using concentrated hydrochloric acid while cooling externally with cold water and stirring vigorously. Subsequently it was heated to 75° C. 1403 g (16.7 mol) of a 50% by weight aqueous cyanamide solution (Degussa-Cyanamide L 500) was added uniformly over a period of 90 minutes while stirring vigorously at an internal temperature of 75 to 80° C. After the cyanamide addition was completed, the reaction mixture was stirred for a further 2 hours at an internal temperature of 75° C. After cooling to 5° C., the crystalline reaction product that can be readily filtered was suction filtered, washed three times chloride-free with 1250 ml water in each case and dried in a vacuum-drying cabinet at 40° C. and 20 mbar. The yield was 1897 g creatine monohydrate (corresponds to a yield of 76.2% of theory).

The invention claimed is:

1. A process for producing creatine monohydrate, comprising:
   (a) dehydrogenating N-methylethanolamine in an alkaline solution, in the presence of a catalyst to form a sodium sarcosinate solution,
   (b) adjusting said sodium sarcosinate solution to a pH of from 7.0 to 13.0 via an acid or bipolar electrodialysis, to form sarcosine, and
   (c) treating said sarcosine with a guanylating agent to form creatine monohydrate,
      wherein the individual reaction steps are carried out without isolating the intermediate products.

2. A process for producing guanidinoacetic acid, comprising:
   (a) dehydrogenating ethanolamine in an alkaline solution in the presence of a catalyst to form a sodium glycinate solution,
   (b) adjusting said sodium glycinate solution to a pH of from 7.0 to 13.0 via an acid or bipolar electrodialysis, to form glycine, and
   (c) treating said glycine with a guanylating agent to form guanidinoacetic acid,
      wherein the individual reaction steps are carried out without isolating the intermediate products.

3. The process of claim 1 or 2, comprising dehydrogenating said N-methyethanolamine or ethanolamine at a pressure of from 0.01 to 30 bar.

4. The process of claim 3, wherein said pressure is from 0.1 to 20 bar.

5. The process of claim 3 wherein said pressure is from 1.0 to 10 bar.

6. The process of claim 3, comprising dehydrogenating said N-methylethanolamine or ethanolamine at a temperature of from 120° C. to 220° C.

7. The process of claim 1, wherein said catalyst is copper, nickel, palladium or platinum.

8. The process of claim 7, wherein said catalyst is present in a supported form.

9. The process of claim 7, wherein said catalyst is present in doped form.

10. The process of claim 1 or 2, wherein said sodium sarcosinate solution or sodium glycinate solution is present at a concentration of from 20% to 65% by weight.

11. The process of claim 10, wherein said sodium sarcosinate solution or sodium glycinate solution is present at a concentration of from 30% to 45% by weight.

12. The process of claim 1 or 2, further comprising removing said catalyst before step (b).

13. The process of claim 1 or 2, comprising adjusting said pH with an acid selected from the group consisting of nitric acid, phosphoric acid, acetic acid, hydrochloric acid, sulfuric acid, and carbon dioxide.

14. The process of claim 1 or 2, further comprising re-feeding an alkaline product produced in step (b) into step (a).

15. The process of claim 1 or 2, wherein step (c) is carried out at a pressure of from 0.1 to 10 bar.

16. The process of claim 15, wherein said pressure is from 1.0 to 5.0 bar.

17. The process of claim 1 or 2, wherein said step (c) is carried out at a temperature of from 10° C. to 120° C.

18. The process of claim 17, wherein said temperature is from 20° C. to 80° C.

19. The process of claim 1 or 2, wherein said guanylating agent is O-alkylisourea or a salt thereof, or S-alkylthiourea or a salt thereof, or cyanamide.

20. The method of claim 1 or 2, wherein said sodium sarcosinate sodium glycinate, sarcosine or glycine is present at a ratio of from 1:0.1 to 1: to 2.0 relative to said guanylating agent.

21. The process of claim 20, wherein said ratio is from 1:1.0 to 1:1.1.

22. The process of claim 1 or 2, wherein said process is continuous.

23. The process of claim 1 or 2, further comprising washing said creatine monohydrate or guanidinoacetic acid with aqueous medium.

24. The process of claim 1, further comprising drying said creatine monohydrate to form creatine.

* * * * *